United States Patent [19]

Macovski

[11] Patent Number: 4,578,803
[45] Date of Patent: Mar. 25, 1986

[54] ENERGY-SELECTIVE X-RAY RECORDING AND READOUT SYSTEM

[76] Inventor: Albert Macovski, 2505 Alpine Rd., Menlo Park, Calif. 94025

[21] Appl. No.: 590,533

[22] Filed: Mar. 16, 1984

Related U.S. Application Data

[63] Continuation of Ser. No. 327,770, Dec. 7, 1981, abandoned.

[51] Int. Cl.[4] .......................... A61B 6/00; G01N 23/04
[52] U.S. Cl. ........................................ 378/62; 378/156
[58] Field of Search ................... 378/185, 44, 62, 156, 378/5; 250/482.1

[56]    References Cited
U.S. PATENT DOCUMENTS 2,541,599   2/1951   Morrison ............................. 378/156

3,860,817   1/1975   Carmean .............................. 378/62

Primary Examiner—Alfred E. Smith
Assistant Examiner—T. N. Grigsby
Attorney, Agent, or Firm—Townsend and Townsend

[57]    ABSTRACT

Energy-selective x-ray images are produced using two scintillating screens separated by an x-ray hardening filter. Photosensitive surfaces individually receive the light images from each screen. The resultant image transparencies are read out optically using a partially reflecting mirror between the transparencies and detecting the reflected and transmitted light. The x-ray spectral separation between the two acquired images can be further increased by using an x-ray source filter having a K-absorption edge in the vicinity of the region of overlap of the two spectra.

4 Claims, 12 Drawing Figures

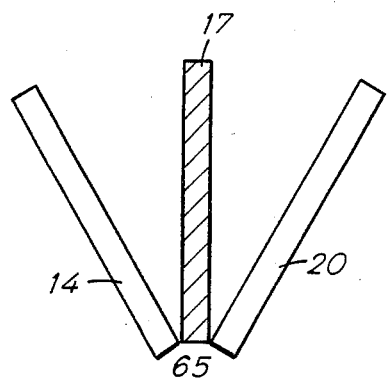
FIG. 7
FIG. 8
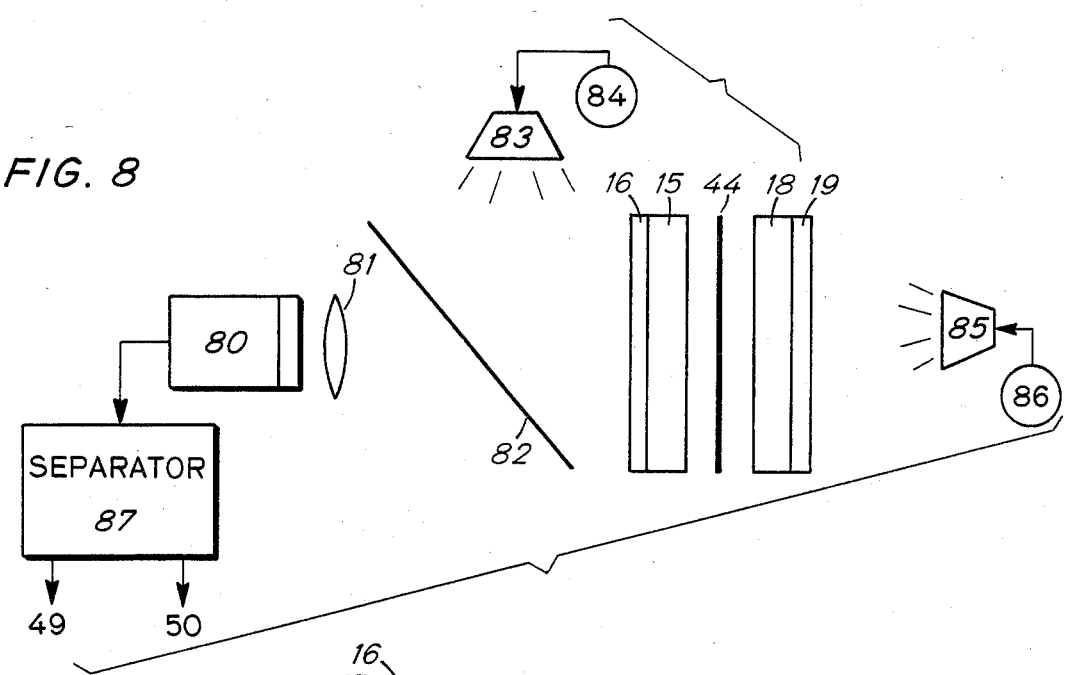
FIG. 9
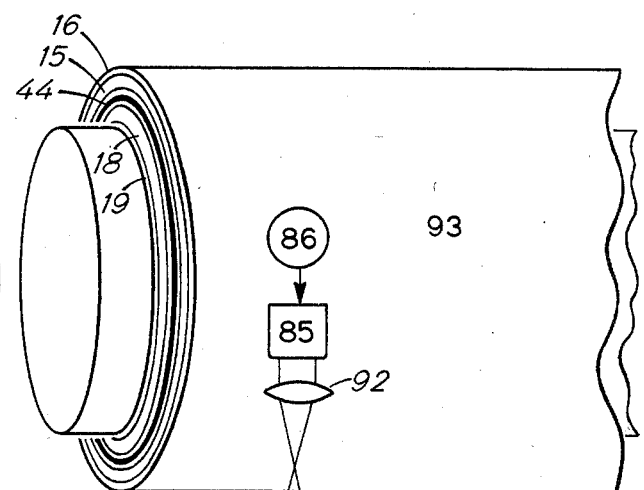
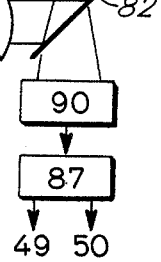

ENERGY-SELECTIVE X-RAY RECORDING AND READOUT SYSTEM

This is a continuation of application Ser. No. 327,770, filed Dec. 7, 1981, and now abandoned.

BACKGROUND OF THE INVENTION

1. Field of the Invention

This invention relates to x-ray imaging systems. In a primary application the invention relates to diagnostic x-ray systems where selected images are created representing specific body materials.

2. Description of Prior Art

In U.S. Pat. No. 4,029,963 issued to R. E. Alvarez and A. Macovski a method was described of acquiring and processing x-ray images at two energy spectra. The processed images can subsequently be used to selectively image various body materials. In the referenced patent two photosensitive emulsions are exposed using two scintillating screens. One problem with the system shown is that of achieving sufficient separation of the two energy spectra used to obtain the two acquired images. When these spectra have significant spectral overlap, with relatively small separation in the average energies, the resultant processed images have poor signal-to-noise ratio.

Another problem with the method shown in that patent is that of registration. In the system shown, the films representing each energy spectrum are scanned independently. This can often result in misregistration with the processed images becoming distorted. This registration problem was solved in pending patent application Ser. No. 299,208, filed Sept. 3, 1981 "X-Ray Encoding Systems Using an Optical Grating" invented by R. E. Alvarez, A. Macovski and B. Strul. In that application the information is encoded using an optical grating. Here the two images are represented by different spatial frequencies and can thus remain perfectly registered. In this system, however, the readout operation requires resolving the very high spatial frequencies of the optical gratings. Thus much of the resolution capacity of the optical scanner is used for the grating frequencies.

SUMMARY OF THE INVENTION

An object of this invention is to provide a method of acquiring x-ray projection data onto photographic film at different x-ray spectra with good spectra separation.

It is a further object of this invention to provide a method for reading out the acquired data in good registration without requiring excess spatial resolution.

It is a further object of this invention to provide a dual film system which enables data acquisition with good spectral separation and readout in good registration.

Briefly, in accordance with the invention, individual films are used with two scintillating screens to acquire the low and high energy image data. A beam-hardening filter is placed between the two screens to increase the spectral separation of the two acquired images. An additional x-ray filter is used at the x-ray source having a K-absorption edge in the region of spectral overlap to increase the spectral separation. The individual films are joined at at least one edge to assure registration on readout. A partially silvered mirror is placed between them and they are scanned with a light beam. The transmitted light represents the sums of the two film densities while the reflected light represents the density of the first film only. The resultant signals are processed to provide individual representations of the high and low energy acquired data.

BRIEF DESCRIPTION OF THE DRAWINGS

For a more complete disclosure of the invention reference may be made to the following description of several illustrative embodiments thereof which is given in conjunction with the accompanying drawings, of which:

FIG. 7 is an embodiment of a dual screen system;

FIG. 8 is an alternate embodiment of a readout system using a television camera; and FIG. 9 is an alternate embodiment of a readout system using a drum scanner.

DESCRIPTION OF THE PREFERRED EMBODIMENT

Figure 2:
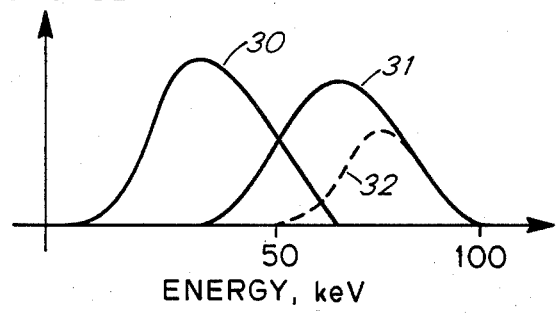
FIG. 2 illustrates graphs describing the performance of the invention.

An understanding of the broad aspects of the invention may best be had by reference to FIG. 2 of the drawings. It is desired to make selective projection images of specific materials of object 10, usually the human anatomy, by making measurements at two energy spectra and processing the measurements. As shown, an x-ray beam 12, produced by source 11 is projected through object 10 onto a parallel array consisting of scintillating screens 14 and 20, substrates 15 and 18 with their respective photosensitive surfaces 16 and 19, and an optically opaque x-ray filter 17. As described in the prior art, the lower energy x-rays are selectively absorbed in the first screen 14 with the higher energy x-rays passing on to screen 20. The light from these screens is recored on photosensitive surfaces 16 and 19 respectively.

FIG. 2 illustrates typical response spectra for the two screens as graph 30 for screen 14 and graph 31 for screen 20. As is seen the lower energy graph 30 and the higher energy graph 31 have considerable overlap. This reduces the separation in their average energies and seriously limits the ability of subsequent processing systems. The net result is poor signal-to-noise ratio in the resultant processed selected images.

This problem is greatly alleviated by using x-ray filter 17 between the two screens. This filter can be designed to increase the spectral separation. For example, filter 17 can be an x-ray beam-hardening material, such as copper, which selectively absorbs lower energies. As shown in the dashed line in FIG. 2, graph 32 illustrates the response of screen 20 with the beam-hardening filter 17. The separation is significantly increased, resulting in improved signal-to-noise ratio. The thickness and material used in filter 17 are a compromise between spectral separation and the attenuation of the desired higher energy x-ray photons. In addition, filter 17 should be optically opaque to prevent optical cross talk where the light produced by the two screens would reach the opposite photosensitive surface. Clearly a unique type of film system is required to enable insertion of filter 17, as will be subsequently discussed.

Figure 3:
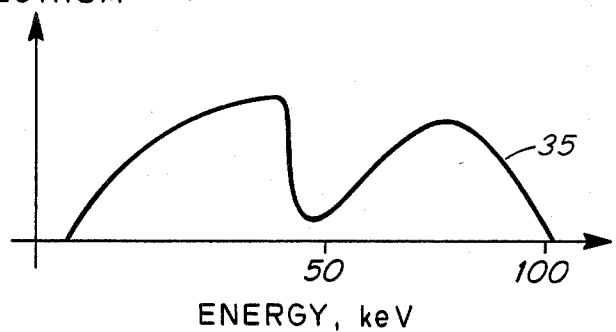
FIG. 3 illustrates another graph describing the performance of the invention.

To further provide spectral separation filter 13 is placed between the x-ray source 11 and object 10. This filter has a K-absorption edge in the vicinity of the region of overlap between the two spectra. The graph of the transmitted spectra of this filter is illustrated in FIG. 3. As shown, the K-absorption edge attenuates the region of overlap, thus providing further spectral separation. Representative materials having K edges in this region are the rare earths such as europium and gadolinium, and other materials such as tungsten and tantalum. One desirable characteristic of the filter is attenuation of the tungsten characteristic emission lines from the x-ray source. These tend to reduce the spectral separation.

Figure 4:
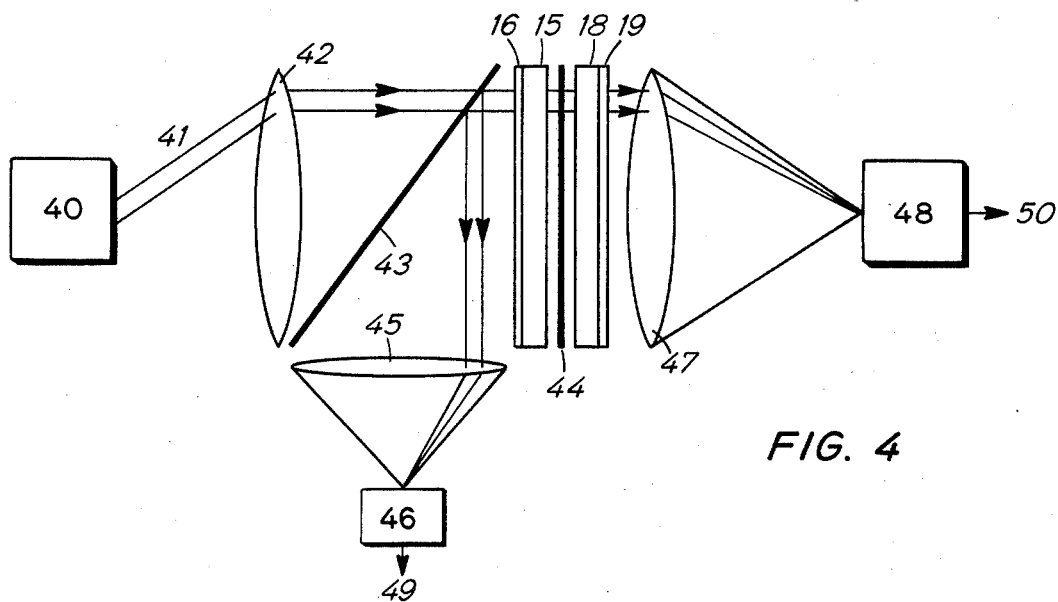
FIG. 4 is a schematic illustration of an embodiment of a readout system.

Having recorded separable spectral information on the two photosensitive surfaces 16 and 19, we must now read them out, after a suitable image development process where photosensitive emulsions 16 and 19 become transparencies. This is accomplished, as shown in FIG. 4, by placing a partially reflecting mirror 44 between substrates 15 and 18. Here again the unique configuration of the film system, to be described, enables the partially reflecting mirror to be inserted. This mirror can consist of a metallic layer on some substrate such as mylar. The metal film can be sandwiched between two plastic layers to protect it from scratching.

The partially reflecting mirror enables the readout to two signals; a first signal due to light passing through transparency 16, being reflected by mirror 44 and passing back through transparency 16 and being detected by detector 46, and a second signal due to light passing through transparency 6, mirror 44 and transparency 19 and being detected by detector 48. Thus the signal detected by detector 46 represents the first transparency and the signal detected by detector 48 represents the product of both transparencies. Appropriate processing can provide signals representing each transparency. In this way the data is read out with a single light beam, insuring perfect registration. Systems can be used with fully reflecting mirrors and separate scanning beams on each side reading the individual transparencies. These, however, would suffer from potential misregistration problems.

Taking a detailed study of FIG. 4, light beam scanner 40, preferably a laser scanner, produces scanned light beam 41. This is collimated using lens 42. The collimated beam passes through partially reflecting mirror 43 through transparency 16 onto partially reflecting mirror 44. The light reflected from 44 goes back through transparency 16, is reflected by partially reflecting mirror 43 onto collecting lens 45 where it is concentrated onto photocell detector 46 to provide signal 49. The light transmitted by mirror 44 passes through transparency 19 and is collected by collecting lens 45 and concentrated onto photocell detector 48 to form signal 50. These scanned signals, 49 and 50, define the information stored on the two transparencies.

Figure 4A:
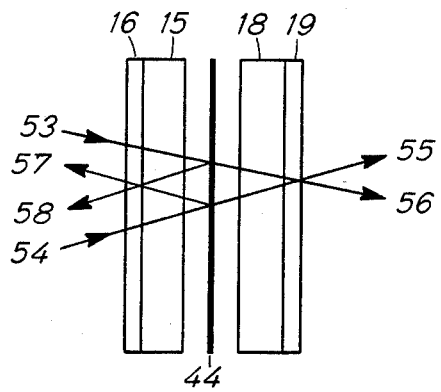
FIG. 4a is a closeup of a portion of the readout system.

FIG. 4a is a detailed look at an embodiment of a focusing system. Here the incoming scanned light beam is represented by converging rays 53 and 54. These are transmitted through mirror 44 and focus on transparency 19, then diverge to form rays 55 and 56 where they go on to detector 48. The rays reflected from mirror 48 focus onto transparency 16, then diverge to rays 57 and 58 where they go on to detector 46. Thus the detected signals include focused components of both transparencies.

Figure 1:
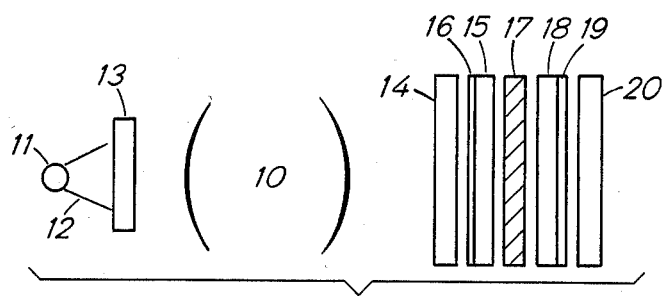
FIG. 1 is a schematic illustrating an embodiment of the invention.
Figure 5A:
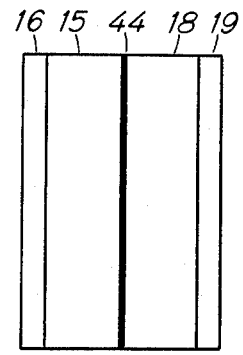
FIG. 5a, 5b and 5c are alternate embodiments of dual film systems.

The photosensitive substrates 16 and 19 and their substrates 15 and 18 can be used in a variety of configurations. In FIG 5a the partially reflecting mirror 44 is bonded to the substrates to form a single bonded sandwich of the various layers. This sandwich can be used in the scanner of FIG. 4 and in the subsequently described scanners of FIGS. 8 and 9. It cannot, however, be used in the system of FIG. 1 where an x-ray filter 17 is placed between the photosensitive surfaces. It therefore cannot use that mechanism of improved spectral separation because of its bonded nature. However, the spectral separation mechanism of x-ray filter 13 can continue to be used.

Figure 5B:
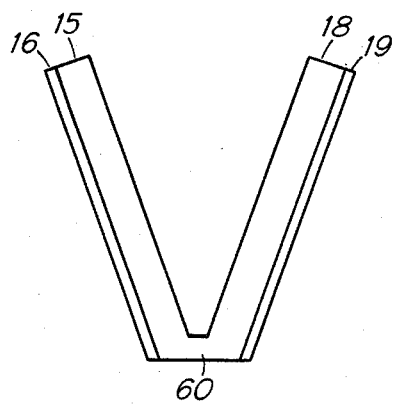

In order to enable the use of x-ray filter 17, a mechanism must be provided of inserting a layer between the substrates 15 and 18. One method is shown in FIG. 5b wherein the substrates 15 and 18 are connected or hinged at one end with connecting section 60. This is simply a plastic connection bonding the films at one end. When the x-ray film is exposed as in FIG. 1, the beam hardening x-ray filter 17 can be placed between substrates 15 and 18. On readout, a partially reflecting mirror 44 is placed between the substrates. The recorded transparencies 16 and 19 remain in perfect registation because they remain connected.

Figure 5C:
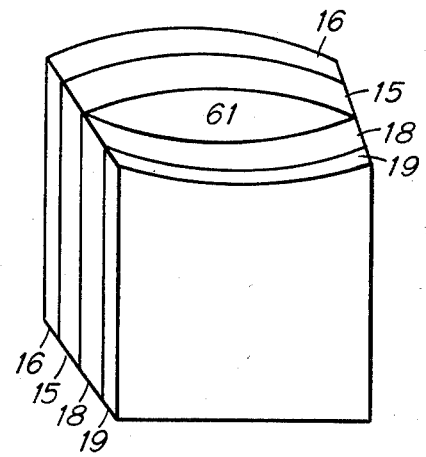

To provide even greater restraint on the relative movement of the individual transparencies the configuration shown in FIG. 5c can be used where the substrates 18 and 19 are joined on three edges, forming an envelope. Here substrates 15 and 18 are connected at every edge except the to. Opening 61 can be used for inserting x-ray hardening filter 17 on recording and partially reflecting mirror 4 when reading. The configurations of 5b and 5c are exemplary of a variety of possibilities which allow insertion of an intermediate layer. For example, the substrates can be joined at two adjacent edges with an open flap, or at specific points around the edges whereby registation of developed transparencies 16 and 19 is maintained.

Figure 6:
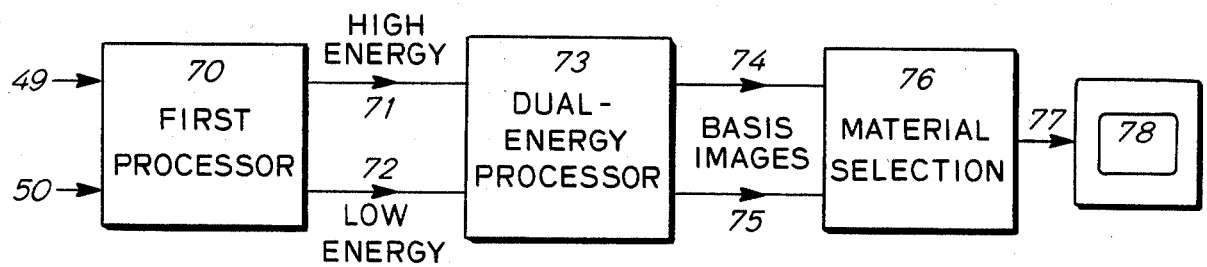
FIG. 6 is a block diagram of the signal processing system used in the invention.

The detected signals 49 and 50 in FIG. 4 are processed as shown in FIG. 6. To a first approximation, the resultant light transmission of each transparency represents the desired log of the x-ray intensity. Thus first processor 70 in FIG. 6 can initailly compensate for nonlinearities in the H-D curve of the film emulsion. In addition, it is desired to provide signals which represent the individual transmissions of each transparency. Signal 49 directly represents the signal due to traversing transparency 16 twice or $\tau_1^2$. Signal 50 represents the transmission through both transparencies $\tau_1 \tau_2$. One method of processing involves taking the square root of signal 49 to provide $\tau_1$, and then dividing signal 50 by $\tau_1$ to provide $\tau_2$. These can then go through appropriate linearity correction to provide signals representing the logs of the high and low energy x-ray intensities, 71 and 72.

These signals are passed on to dual energy processor 73 which is described in the previously referenced U.S. Pat. No. 4,029,963. This processor, using nonlinear combinations of 71 and 72, provides linearized basic images 74 and 75. These can either represent the photoelectric and Compton scattering components, or preferably the equivalent amount of specific materials used in calibration such as aluminum and plastic. Weighted sums or differences of these basic components are taken in 76 to allow a variety of material selection capabilities such as the elimination or enhancement of any material. The selected image is displayed in display monitor 78. FIG. 7 illustrates an embodiment of a cassette used in the x-ray recording process. Here scintillation screens 14 and 20 are hinged, as in existing film-screen cassettes, to facilitate the insertion of a dual emulsion film. In addition, however, the beam-hardening filter 17 is affixed to the hinge 65. This enables the various separated film structures, as shown in FIGS. 5b and 5c, to be placed with filter 17 between the film emulsions. In this way the important energy spectrum separation is enhanced.

FIG. 4 showed a readout system using a single scanning light beam. FIGS. 8 and 9 show another general approach to readout using two light sources. A front light source, on the detector side, illuminates the first transparency with its light reflected by mirror 44 into the detector. A second light source, behind the films, transmits through both transparencies to the detector. These light sources require some type of encoding so that they can be distinguished by the detector. This encoding can be temporal, spatial, color, polarization, etc.

In FIG. 8 front light source 83 is driven by generator 84 with back light source 85 driven by generator 86. The light from 83 is reflected from partially reflecting mirror 82 through transparency 16 and reflected back through transparency 16 from partially reflecting mirror 44. This reflected light is imaged onto TV camera 80 using lens 81. Similarly the light from 85 is transmitted through transparencies 19 and 16 and is imaged onto camera 80 with lens 81.

To separate these signals, the lights 83 and 85 can be turned on alternately using generators 84 and 86. Thus a first frame is scanned by camera 80 representing the reflected light with 83 on and a second frame representing the transmitted light with 85 on. The separator 87, in this case is a video storage system which stores at least the first frame. Thus signals 49 and 50 are generated which, as before, represent the light transmitted and reflected through 16 and the light transmitted through both 19 and 16.

Other encoding systems can be used where the transparencies 16 and 19 are scanned simultaneously. Lights 83 and 85 can be of different colors with camera 80 a color camera. Here signals 49 and 50 would simply represent the different color signals. Also lights 83 and 85 could project different spatial patterns onto the transparencies which could be distinguished by processing the camera output signal. For example, gratings of different frequencies could be projected with separator 87 consisting of filters which separate the two frequencies representing the two transparency combinations. Generators 84 and 86 can also be high frequency signals which turn the lights on and off at a relatively high rate. In that case camera 80 must be a non-storage instantaneous camera such as an image dissector to produce the high frequency signals which distinguish the two sources of illumination.

Since some television cameras have limited resolution capability, FIG. 9 illustrates the same system applied to a drum scanner where relatively high resolution can be realized. Here the sandwiched layers of the two substrates 15 and 18 with the intermediate reflector 44 are wound around rotating drum 93. Light source 85 and lens 92 are inside the drum. They are fixed so that they do not rotate or translate with the drum. The light from 85 is focused onto the transparencies 16 and 19 using lens 92. Similarly the light from source 83 is reflected off partially reflecting mirror 82 and focused onto the transparencies using lens 91. The resultant light from both sources, after interacting with the transparencies, passes through mirror 82 onto detector 90. The signal from detector 90 is passed through signal separator 87 which, as before, provides signals 49 and 50 representing the individual light sources.

The encoding, as before, can be achieved by alternately turning lights 85 and 83 on and off using generators 86 and 84 respectively. This should be accomplished at the rate new picture elements are scanned past the focal region. Separator 90 will alternately switch the detector output to 49 and 50 to provide the required signal separation. Filters can be used to remove the high frequency switching components. As before the light sources can have different colors with detector 90 being a dual detector with different color filters on each photocell. Each output will then directly provide the separable signals 49 and 50.

Systems of this type often require a high degree of accuracy. The separation of the signals from the two transparencies is based on assumed properties of the partially reflecting mirror 44. To insure that variations in the reflectivity and transmission of the mirror do not cause errors, it can be scanned, with any of the systems shown, in the absence of the transparencies 16 and 19 on substrates 18 and 15. Any variations can be recorded and stored. These can be used to correct signals 49 and 50 to avoid errors in the reproduced selective material images.

It should be emphasized that the readout systems shown in FIGS. 4, 8 and 9 have the special quality of automatic perfect registration of the two transparencies. A variety of alternate scanning systems can be used which do not provide automatic perfect registration. These can, however, provide adequate registration if care is taken. For example, if the transparencies can be opened up, as in the configuration of FIG. 5b, they can be scanned separately or in sequence. Registration marks can be placed on each transparency to electronically identify the relative position of the two transparencies.

If the configuration of FIG. 5c is used, a dual fully reflecting mirror can be inserted between the substrates 15 and 18. In that case the individual transparencies can be scanned individually or in sequence from each side. These methods, however, do not have the automatic registration features of the previously described system.

What is claimed is:

1. In a method for acquiring x-ray image data at two energy spectra the steps of:
    exciting a first scintillating screen directly with an x-ray beam having an energy less than 150 kev that has been projected through a body and coupling the light scintillations to a first photographic emulsion;
    filtering the x-ray beam after passing through the first scintillating screen to selectively attenuate a first region of the x-ray spectrum and to permit transmission of a second region of the x-ray spectrum; and
    exciting a second scintillating screen directly with the filtered x-ray beam and coupling the light scintillations to a second photographic emulsion.

2. The method as described in claim 1 wherein the step of filtering the x-ray beam includes the step of hardening the x-ray beam by selectively attenuating the lower energy region of the spectrum.

3. Apparatus for providing x-ray energy selective light images from an x-ray beam under 150 kev comprising:
   a first scintillating screen adapted to be directly excited by and to allow transmission therethrough of an x-ray beam;
   a second scintillating screen adapted to be directly excited by the x-ray beam transmitted by the first screen;
   an optically opaque x-ray filtering layer between the first and second scintillating screens for selectively attentuating different x-ray energies; and
   means for separating the two screens and the optically opaque layer to permit a first substrate with a photosensitive surface to be inserted between the first scintillating screen and the optically opaque x-ray filtering layer and a second substrate with a photosensitive surface surface to be inserted between the second scintillating screen and the optically opaque layer.

4. Apparatus as recited in claim 3 wherein the optically opaque x-ray filtering layer is an x-ray beam hardening filter which selectively attenuates the lower energy x-rays.

* * * * *